United States Patent [19]

Webster

[11] 4,304,257

[45] Dec. 8, 1981

[54] VALVE WITH FLEXIBLE SHEET MEMBER

[75] Inventor: Milo E. Webster, Braintree, Mass.

[73] Assignee: Instrumentation Laboratory Inc., Lexington, Mass.

[21] Appl. No.: 165,103

[22] Filed: Jul. 1, 1980

[51] Int. Cl.³ .............................................. F16K 7/16
[52] U.S. Cl. .................................. 137/559; 137/597; 137/884; 251/331
[58] Field of Search ............... 137/559, 597, 861, 884; 251/61.1, 331

[56] References Cited

U.S. PATENT DOCUMENTS

| 365,767 | 6/1887 | Zilles | 251/331 X |
| 1,793,396 | 2/1931 | Haentjens | 251/331 X |
| 2,865,402 | 12/1958 | Miller | 137/559 X |
| 3,613,729 | 10/1971 | Dora | 251/331 X |
| 3,934,611 | 1/1976 | Gachot | 251/61.1 X |
| 3,951,167 | 4/1976 | Howell | 251/331 X |
| 3,963,440 | 6/1976 | Stein | 422/63 |

FOREIGN PATENT DOCUMENTS

1211752 3/1960 France ................................ 251/331

Primary Examiner—Robert G. Nilson

[57] ABSTRACT

A valve that is particularly useful in biological fluid handling systems includes a body member that has a firm and stable support surface and a flexible sheet member that has a surface for conforming and mating engagement with the surface of the valve body member. A land portion in the surface of one of the valve members separates two fluid flow channels in that member. An actuator is arranged to flex the sheet member between a first position in which the surface of the sheet member is in mating and sealing engagement with the surface of the body member to sealing block flow between the two channels, and a second position in which the sheet surface is spaced from the first position to allow fluid flow across the land surface between the two flow channels.

33 Claims, 16 Drawing Figures

VALVE WITH FLEXIBLE SHEET MEMBER

This invention relates to valves and to flow network arrangements that have particular applications in systems for handling biological fluids and the like.

The design of valves and flow systems for handling biological fluids such as blood involves specialized considerations. For example, valves and systems for handling different fluids or successive samples should be easily cleaned to avoid cross-contamination. Portions of such fluid flow systems must be capable of reliable isolation. As limited quantities of fluids are frequently involved, valves and flow system arrangements should have capabilities of handling and controlling small fluid volumes. Also, biological fluids frequently contain fragile and easily damaged cellular components. An example of a flow network arrangement to which the invention relates is in an instrument for the analysis of specific constituents of biological fluids such as whole blood, serum, and plasma. Such analyses provide useful diagnostic information on metabolic disturbances, and assist in the control of life support devices and the evaluation of the effectiveness of therapeutic measures.

In accordance with the invention, there is provided a valve that is particularly useful in biological fluid handling systems. The valve includes a body member that has a firm and stable support surface and a flexible sheet member that has a surface for conforming and mating engagement with the surface of the valve body member. A land portion in the surface of one of the valve members separates two fluid flow channels in that member. An actuator is arranged to flex the sheet member between a first position in which the surface of the sheet member is in mating and sealing engagement with the surface of the body member to sealing block flow between the two channels, and a second position in which the sheet surface is spaced from the first position to allow fluid flow across the land surface between the two flow channels.

The invention permits the formation of a number of different valve configurations, including "flow through" valve "T" valves, and valves of bypass configurations, and the arrangement of such valves in compact arrays. A particular valve embodiment permits introduction of a gas (i.e., air) for segmenting of a liquid in a flow network. Flow transitions imposed by rapid cycling of the valve provide effective cleaning action. The valve provides excellent isolation between different liquids, which, in a particular embodiment, include successive samples, calibration liquids and conditioning liquids. While valves and flow system arrangements in accordance with the invention have application in a wide variety of fields, particular applications are in systems for the analysis of biological fluids, and in vascular interface systems which provide support for transducers, catheters, sampling sites and the like for ongoing on-line analysis with capability for manual or remote control options. The configuration of the actuator and its direction of movement may vary depending on the particular application. Numerous different actuator systems including electrical, electromechanical, pneumatic and hydraulic may be suitable, also depending on the particular system and application. Similarly, the actuator may be coupled to the valve sheet membrane in various manners, such as a magnetic coupling arrangement with a component embedded in the membrane.

In preferred embodiments, the valve is of biologically compatible materials, and has a small volume (less than ten microliters) when open and essentially zero deadspace when closed. The valve body member is a transparent face plate; at least one of the channels is a groove that extends along the surface of the body member that is engaged by the flexible sheet, and the flexible sheet is opaque and of contrasting color to the fluid to be handled. The actuator flexes the sheet in a direction perpendicular to the support surface to open the valve and form a chamber of generally frustoconical configuration which is filled with the fluid such that an immediate visual indication of the position of the valve is provided. The valve has a gentle and smooth closing action in a radially inward direction which results in significantly less damage to blood cells and similar fragile components of biological fluids then other valves such as face valves that heretofore have been utilized in blood analysis instruments.

In a particular valve array embodiment, the cylindrical head portions of a plurality of actuators are embedded in a relatively soft (less than one hundred Shore A durometer) polyurethane membrane sheet and a flow channel network is formed in a face plate of transparent acrylic plastic. A spring-loaded backing plate clamps the membrane against the face plate and maintains consistent clamping and sealing forces. Each individual valve has a spring which moves its membrane portion into mating engagement with the rigid face plate surface and a solenoid actuator provides axial force to flex the membrane away from the face plate surface with modest stressing of the membrane. Valves in accordance with the invention are easy to fabricate, easy to operate, and may be arranged in compact valve arrays in a variety of fluid handling networks.

Other features and advantages of the invention will be seen as the following description of a particular embodiment progresses, in conjunction with the drawings, in which:

DESCRIPTION OF PARTICULAR EMBODIMENTS

Figure 1:
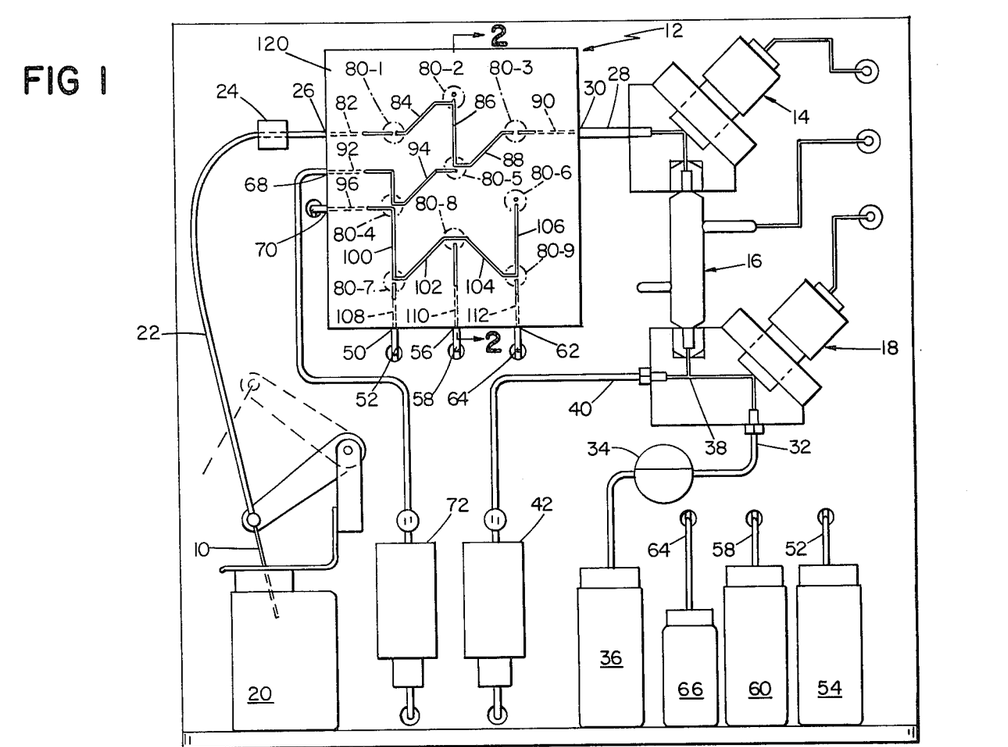
FIG. 1 is a front view of a blood analysis instrument in accordance with the invention.

Shown in FIG. 1 is a front view of a blood analysis instrument that includes a sample probe 10, a valve array 12, a potassium sensing electrode 14, a sodium sensing electrode 16, and a reference electrode 18. Sample probe 10 is movable between a waste receptacle 20 and a sample source. Inlet line 22 is connected between sample probe 10 and inlet 26 of the valve array. Rigid tube 28 is connected between valve array outlet 30 and the potassium sensing electrode 14. Connected to reference electrode 18 through line 32 and pinch valve 34 is a source 36 of reference electrolyte. Line 40 from reference electrode assembly 18 is connected through peristaltic pump 42 to waste receptacle 20.

Valve array 12 also has an inlet 50 connected via line 52 to a first source 54 of calibrating fluid; an inlet 56 connected via line 58 to a second source 60 of calibrating fluid; a third inlet 62 connected via line 64 to a source 66 of conditioner for the sodium electrode 16; and ports 68, 70 connected to peristaltic pump 72.

The valve array 12 includes nine valves 80 and an array of interconnecting passages; passage 82 extending from port 26 to valve 80-1; passage 84 extending from valve 80-1 to valve 80-2; passage 86 extending from valve 80-2 to valve 80-5; passage 88 extending from valve 80-5 to valve 80-3; passage 90 extending from valve 80-3 to outlet port 30; passage 92 extending from port 68 to valve 80-4; passage 94 extending from valve 80-4 to valve 80-5; passage 96 extending from valve 80-4 to port 70; passage 100 extending from valve 80-4 to valve 80-7; passage 102 extending from valve 80-7 to valve 80-8; passage 104 extending from valve 80-8 to valve 80-9; passage 106 extending from valve 80-9 to valve 80-6; passage 108 extending from valve 80-7 to port 50; passage 110 extending from valve 80-8 to port 56; and passage 112 extending from valve 80-9 to port 62.

Figure 2:
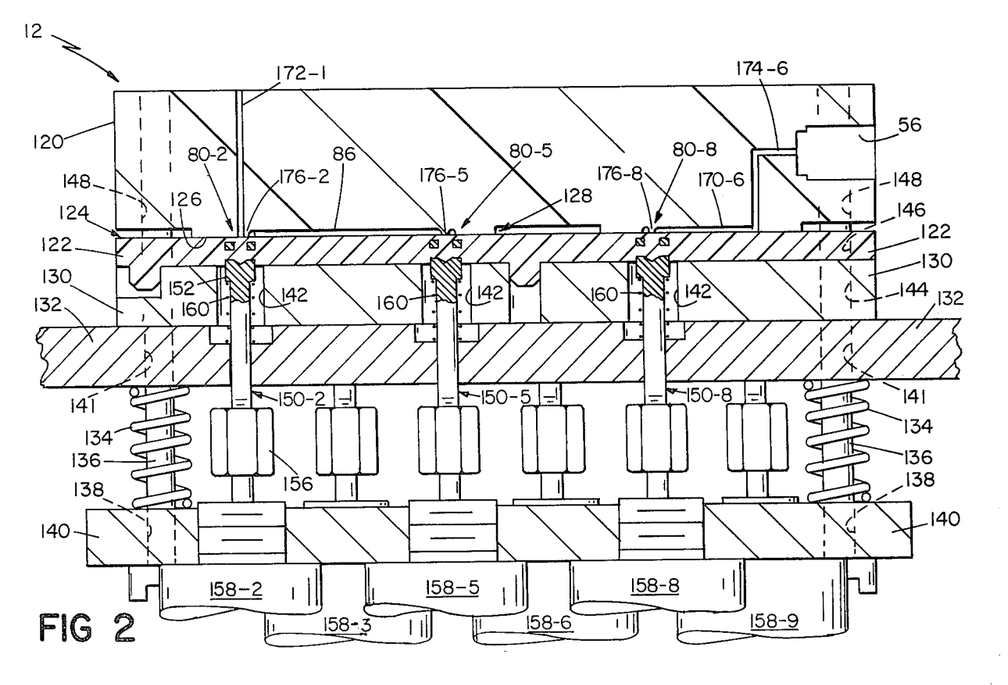
FIG. 2 is a sectional view, taken along the line 2—2, of the valve array employed in the instrument shown in FIG. 1.
Figure 3:
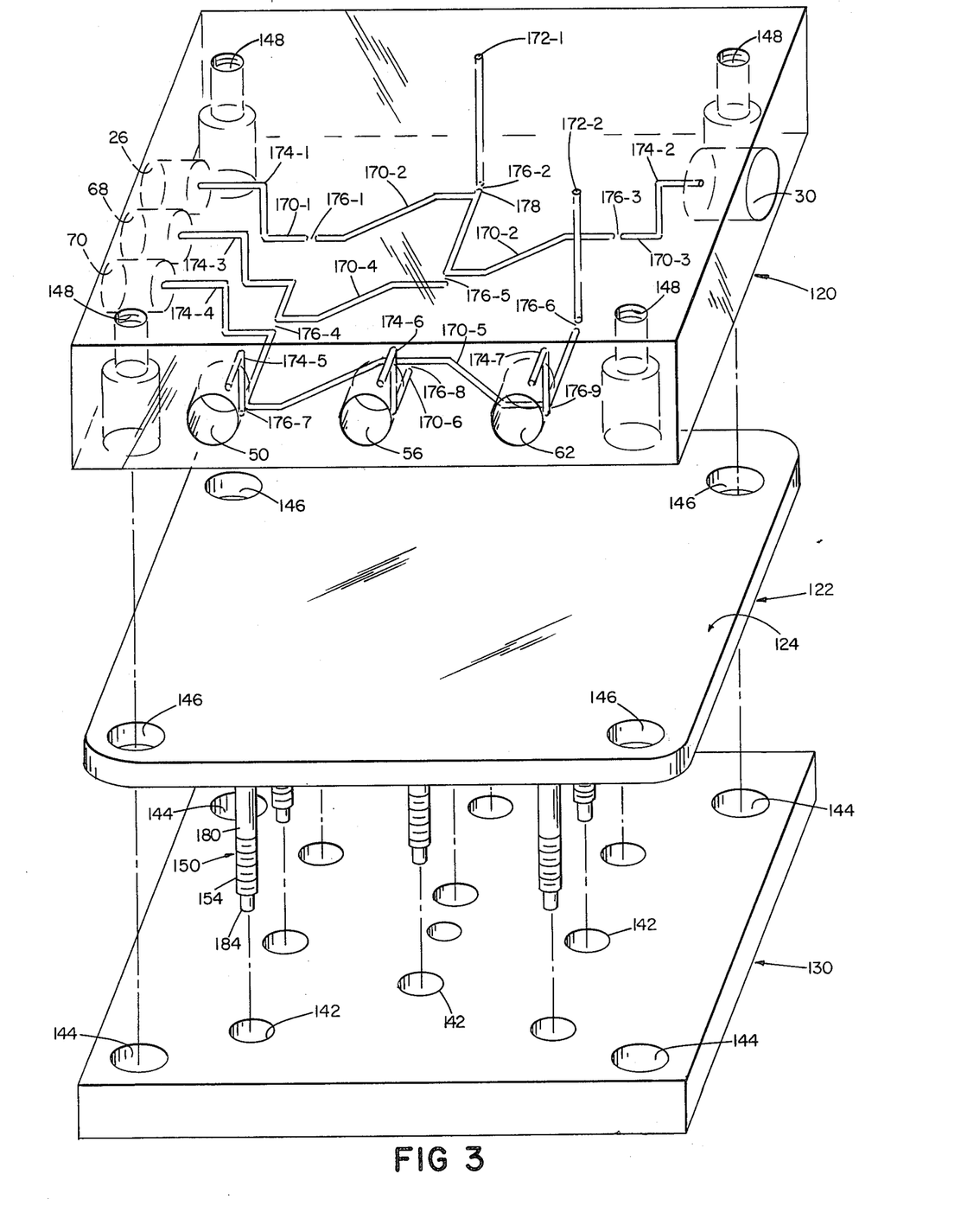
FIG. 3 is an exploded view of components of the valve array shown in FIG. 2.

A sectional view of the valve array 12 is shown in FIG. 2. That valve array includes a transparent face plate 120 of cast acrylic resin that has a width of about eight centimeters, a length of about 8½ centimeters, and a depth of about 1½ centimeters. Clamped against the bottom surface of face plate 120 is a manifold diaphragm sheet 122 of white polyurethane of 40 shore A durometer hardness that has a smooth, pit-free surface 124 (the mold surface having a mirror polish) seated against the surface 126 of the raised land array 128 (FIG. 4) on the lower surface of plate 120. Diaphragm sheet 122 has a thickness of about three millimeters and its width and length dimensions are slightly less than the width and length dimensions of face plate 120. Apertures aluminum backing plate 130 has a thickness of about six millimeters and the same width and length dimensions as face plate 120. Mounting plate 132 is biased against the bottom of backing plate 130 by springs 134 which are supported on headed studs 136 that pass through holes 138 in solenoid support plate 140 and then through holes 141 in mounting plate 132, holes 144 in backing plate 130, holes 146 in diaphragm sheet 122 and are secured in threaded bores 148 in face plate 120.

Secured to diaphragm member 122 is an array of nine actuators 150, the head 152 of each being embedded in the polyurethane manifold sheet 122. Each actuator 150 is connected by a threaded section 154 and coupling 156 to a solenoid actuator 158. A spring 160 (of about one pound closing force) is seated between surface 162 of plunger 150 and recess 164 of mounting plate 132.

Figure 4:
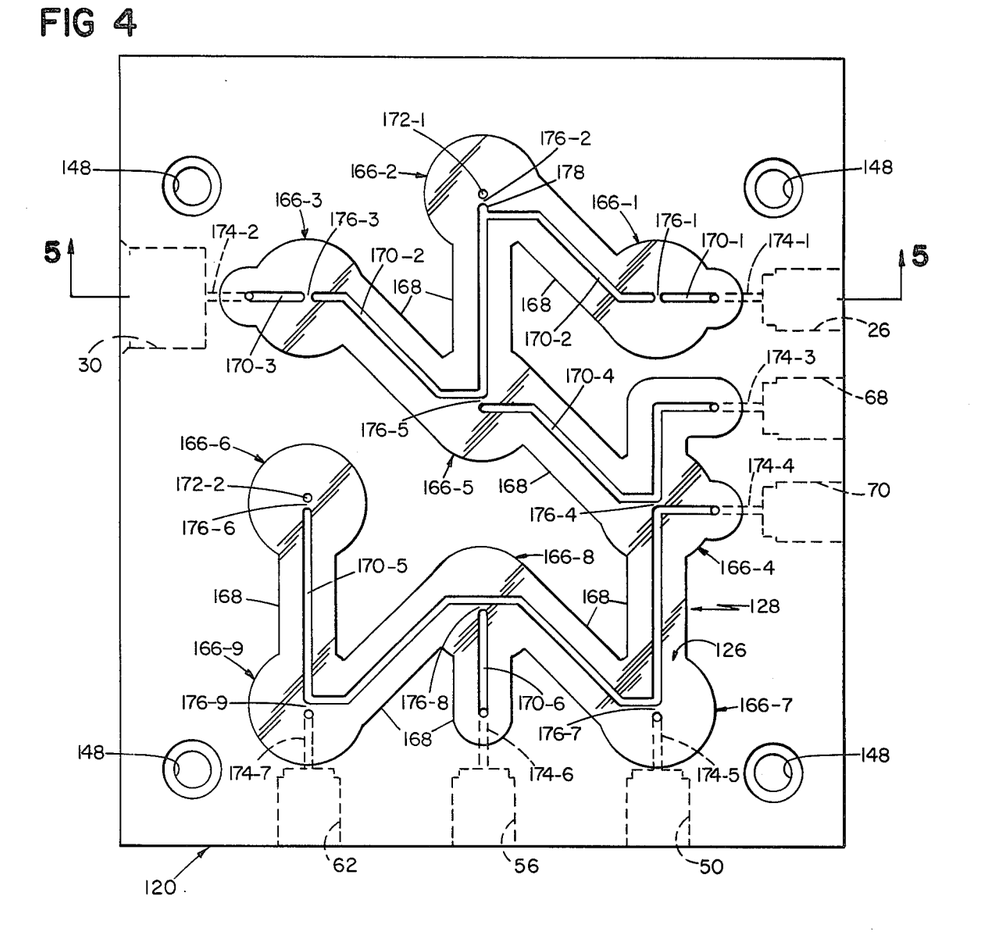
FIG. 4 is an elevational view of the face plate of the valve array showing details of the flow network.
Figure 5:
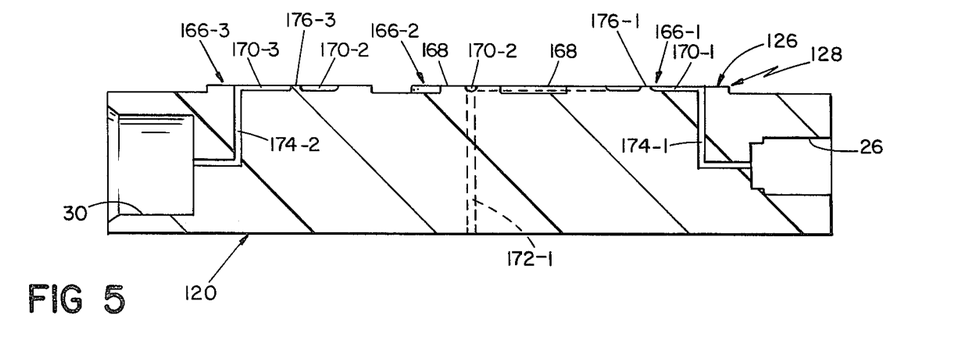
FIG. 5 is a sectional view taken along the line 5—5 of FIG. 4.

Further details of the raised land array 128 in face plate 120 may be seen with reference to FIGS. 4 and 5. Land array 128 includes a set of nine generally circular valve sites 166, each about 1¼ centimeter in diameter, and interconnection lands 168, each about ⅜ centimeter in length. Surface 126 of the land array 128 is about 0.4 millimeter above the base surface of face plate 120 and is flat and smooth (RMS 32). Formed in each valve land and interconnecting land is one or more channels, in the form of grooves or trenches 170 (each about 0.8 millimeter in width and about 0.6 millimeter in depth formed by a ball end mill); through bores 172-1 and 172-2, each about 0.8 millimeter in diameter; and L-shaped passages 174, each of which extends between an external port and a groove in a valve land. Thus, passage 82 extends from port 26 through L-shaped passage 174-1 and groove 170-1 to land 176-1 at valve site 166-1; and groove 170-2 extends from valve site 166-1 through valve sites 166-2 and 166-5 to land 176-3 at valve site 166-3. At each valve site is a valve land 176 about ¼ millimeter in width; land 176-1 separating channels 170-1 and 170-2; land 176-2 separating bore 172-1 from stub extension 178 of channel 170-2; land 176-3 separating the end of channel 170-2 from channel 170-3; land 176-5 separating channel 170-2 from channel 170-4; land 176-4 separating channels 170-4 and 170-5; land 176-6 separating channel 170-5 from bore 172-2; land 176-7 separating channel 170-5 from passage 174-5; land 176-8 separating channel 170-5 from 170-6; and land 176-9 separating channel 170-5 from passage 174-7.

Figure 6:
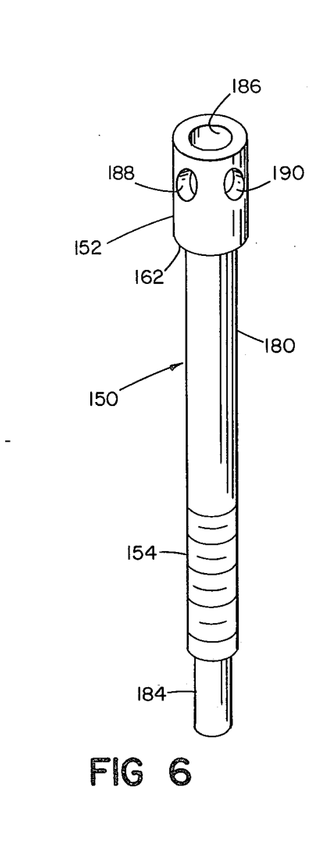
FIG. 6 is a perspective view of a valve actuator rod.

Further details of the valve actuator rod 150 may be seen with reference to FIG. 6. Each rod has a head portion 152 about three millimeters in diameter and about four millimeters in length, a shaft section 180 about two millimeters in diameter with a threaded section 154 about six millimeters in length and a foot portion 184. Formed in head portion 152 is an axially extending bore 186 about 1¾ millimeter in diameter and 2½ millimeters deep; and two transverse bores 188, 190 that extend through head 152 and each is about one millimeter in diameter. The heads 152 of actuator 150 are embedded in the manifold diaphragm 122 during the molding operation with polyurethane flowing through bores 186, 188, and 190 to securely affix the actuator head 152 to the diaphragm sheet 122.

Figure 7:
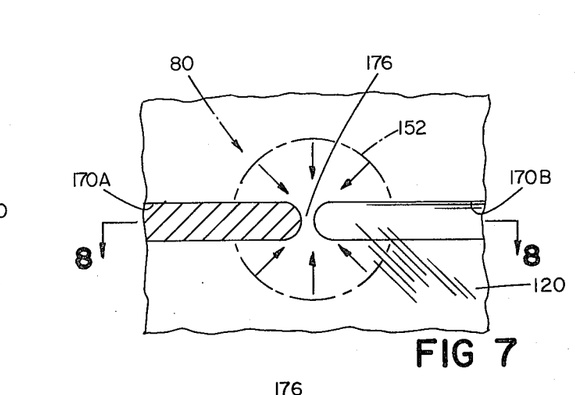
FIG. 7 is a view of a valve in accordance with the invention in closed position.
Figure 8:
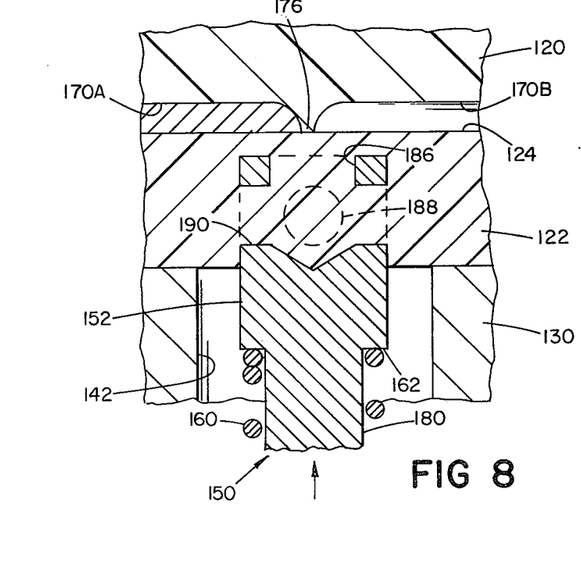
FIG. 8 is a sectional view taken along the line 8—8 of FIG. 7.
Figure 9:
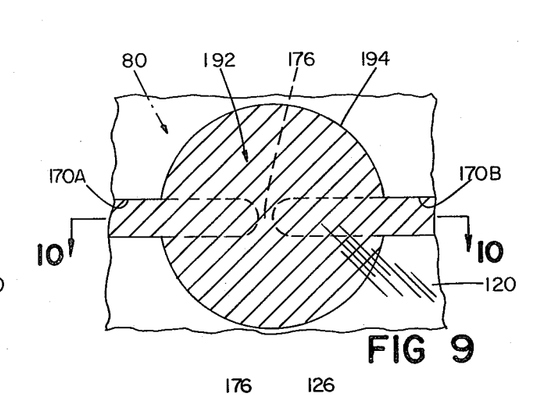
FIG. 9 is a view of the valve of FIG. 7 in open position.
Figure 10:
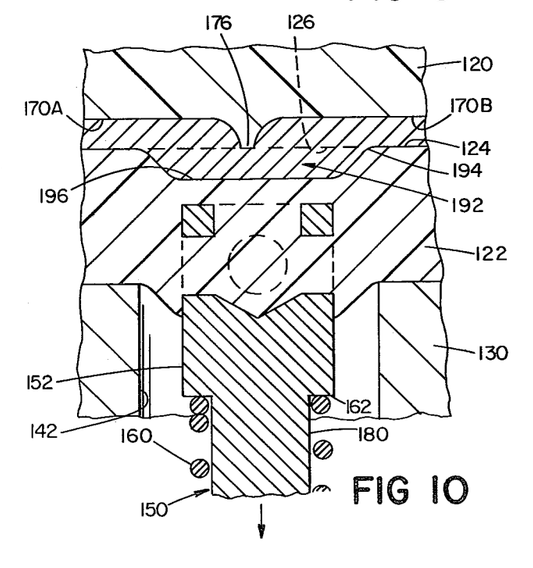
FIG. 10 is a sectional view taken along the line 10—10 of FIG. 9.

Shown in FIGS. 7 and 8 is a view of a valve 80 in closed position with diaphragm surface 124 seated on land 176. The inlet channel 170A is filled with blood (which is visible through transparent face plate 120) but flow to the outlet channel 170B is blocked by the firm seating of diaphragm surface 124 against land 176, in a "zero deadspace" valving action. Movement of actuator 150 by its solenoid 158 (an axial travel of about ¾ millimeter) moves the valve to its fully open position as shown in FIGS. 9 and 10. In that position, a valve chamber 192 of frustoconical configuration is formed over land 176 with a circular peripheral margin 194 in contact with plate surface 126, and a generally flat surface 196 spaced from land 176. The blood from channel 170A flows through chamber 192 to outlet channel 170B, and the fluid color contrast with the white background of diaphragm 122 (a circular area about four millimeters in diameter) provides an indication that is clearly visible through the transparent face plate 120 of the open position of the valve.

When actuator 150 is released, the membrane resilience supplemented by a gentle closing force of spring 160 returns the flexed portion of diaphragm 122 to its initial seated position in a smooth, radial inward, wiping action which flows fluid from the valve chamber 102 into the channels 170A and 170B so that the diaphragm surface 124 gently seats on the plate surface 126 with essentially no damage to delicate cellular material in the fluid being controlled by the valve.

Isolation valves 80-1 and 80-3 are of the type shown in FIGS. 7-10; T-valves 80-5, 80-7, 80-8, and 80-9 have a straight through channel that is always open and a second channel separated from the straight through channel by a valve land; vent valves 80-2 and 80-6 have a channel separated from a perpendicular vent passage via a valve land; and shunt valve 80-4 has two flow through channels separated by a valve land.

Figure 11:
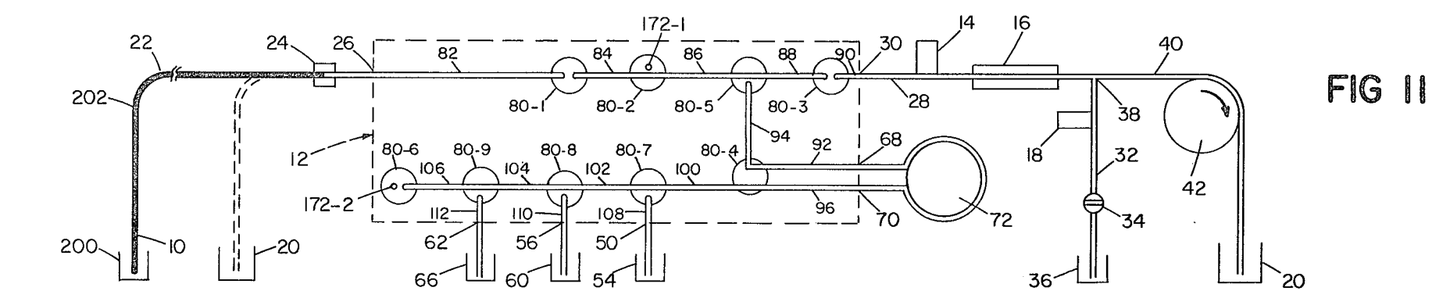
FIGS. 11–16 are diagrams showing operational sequences of the instrument shown in FIG. 1.

An operational sequence of the instrument is indicated in the diagrams of FIGS. 11–16. With the tip of sample probe 10 immersed in a sample of the liquid to be analyzed in container 200, as indicated in FIG. 11, valves 80-1 and 80-3 are opened by their respective solenoids 158-1 and 158-3, and peristaltic pump 42 is operated to inspirate sample 202 through probe 10 to sensor 24. When sensor 24 signals that the desired quantity of sample to be analyzed (about 180 microliter volume of blood or serum) valve 80-1 is closed and valve 80-2 is opened to vent the line between valve 80-1 and pump 42. Pump 42 is then stopped and the sample 202 to be analyzed thus is stored in line 22 as indicated in FIG. 11.

Figure 12:
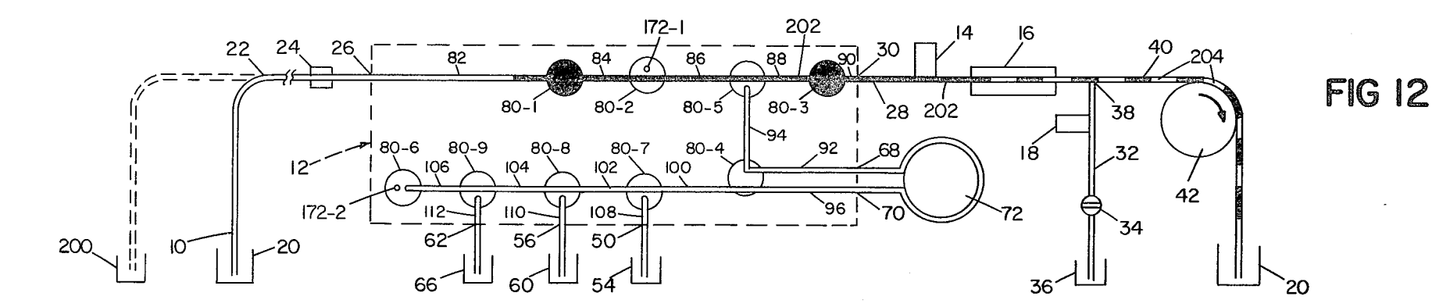
Figure 13:
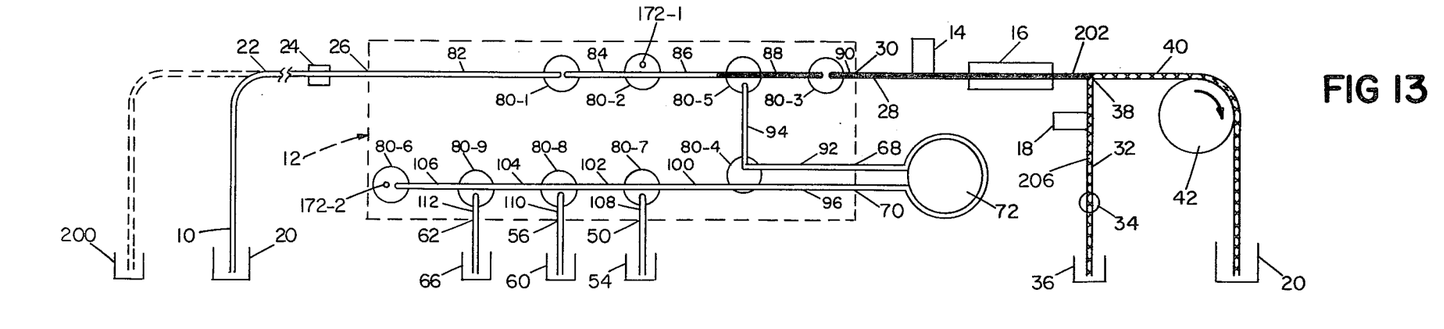

When probe 10 has been wiped and inserted into waste receptacle 20, vent valve 80-2 is closed and probe isolation valve 80-1 is opened, and pump 42 is again energized to draw the sample 202 through the valve array 12 into the sample chambers of electrode systems 14 and 16. As the blood sample 202 is being drawn past valve 80-2, that valve is pulsed seven times, the valve being open for about 40 milliseconds and closed for about 130 milliseconds at each pulse cycle, so that seven segments 204 of air are inserted into the leading portion of sample 202, as indicated in FIG. 12. This segmenting of the blood sample produces liquid flow transients which clean the surfaces of the flow passages and analysis chambers. This segmented leading portion of the blood sample 202 is drawn through the electrode chambers 14 and 16 and past the reference junction 38 and through line 40. Electrode isolation valve 80-3 is closed on the trailing portion of the blood sample 202 as indicated in FIG. 13, so that the blood sample is held in the analysis chambers of potassium electrode 14 and sodium electrode 16. Pinch valve 34 is simultaneously opened and electrolyte 206 is drawn from reservoir 36 past reference electrode 18 and through junction 38 to form a conductive path from reference electrode 18 to the blood sample 202 as indicated in FIG. 13. About one second after valve 34 is opened, pump 42 is stopped and the electrodes 14, 16 are allowed to equilibrate with the sample 202.

Figure 14:
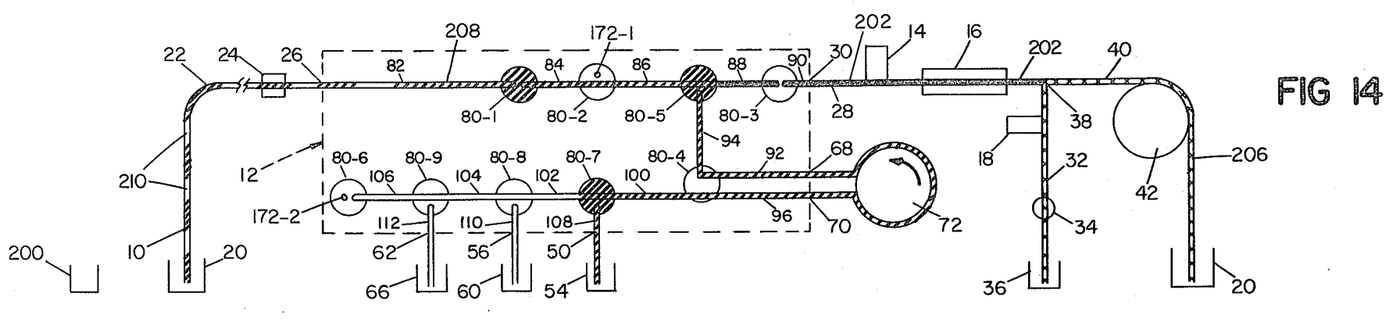

During that equilibration interval, probe 10 is back flushed by means of pump 72. Valves 80-1, 80-5, and 80-6 are opened. With valve 80-4 closed, pump 72 is operated and the manifold line (sections 100, 102, 104, and 106) is dried, the liquid being pumped by pump 72 from the manifold through probe 10 into waste receptacle 20. Calibrate valve 80-7 is then opened and liquid 208 is drawn from reservoir 54 by pump 72 in a back flushing flow through sample probe 10 to waste container 20. During this flush cycle, pulse operation of valve 80-6 introduces segments 210 of air into the leading portion of the flush liquid 208 as indicated in FIG. 14. After the back flush interval, all pumping is stopped for the remainder of the equilibration interval (about eight seconds), and then data is taken from the sodium and potassium electrode systems.

Figure 15:
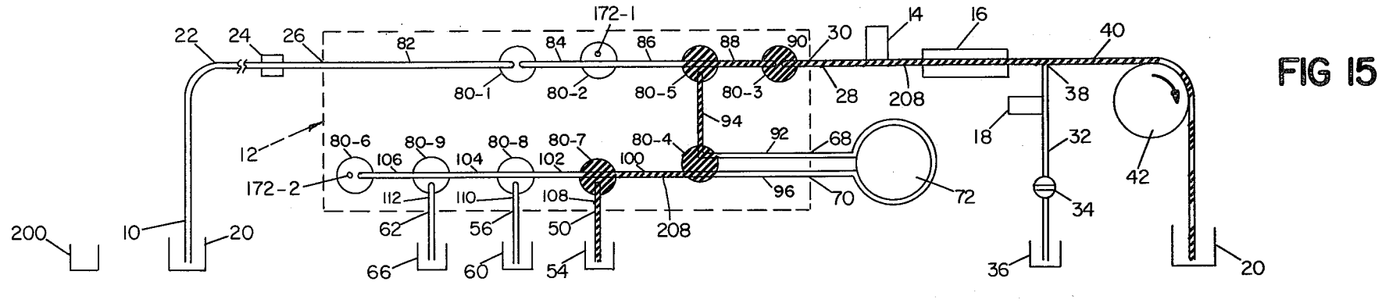

After the data has been taken, the analysis chambers are flushed and a calibration check is run. Valves 80-1 and 80-3 are opened and probe 10 is aspirated dry by pump 42 with concurrent pulsing of valve 80-2 to clean that valve. Valve 80-1 is then closed; valves 80-4, 80-5, and 80-7 are opened; and pump 42 pulls calibrating liquid from reservoir 54 through the sample analysis chambers of electrode systems 14 and 16 as indicated in FIG. 15. This flow of liquid has its leading edge segmented by operation of air valve 80-6 to provide cleaning action of the flow passage surfaces and analysis chambers; and then valve 80-6 is closed so that there is a continuous flow of calibration fluid through the analysis chambers of electrode systems 14 and 16 as indicated in FIG. 15. Valve 80-3 is then closed and valve 34 is opened to create an electrolyte-calibration liquid interface at junctions 38, and the calibration of electrodes 14 and 16 is checked. During the flushing and cleaning cycle of the probe (FIG. 14) and of the analysis chambers (FIG. 15) each valve in the sample flow path (valves 80-1, 80-2, 80-5, and 80-3) is opened and closed in a flutter action which provides effective cleaning of the valve chambers 192. Thus the valves, probe 10, and the analysis chambers of the electrode systems 14 and 16 are cleaned in preparation for the next analysis cycle.

Figure 16:
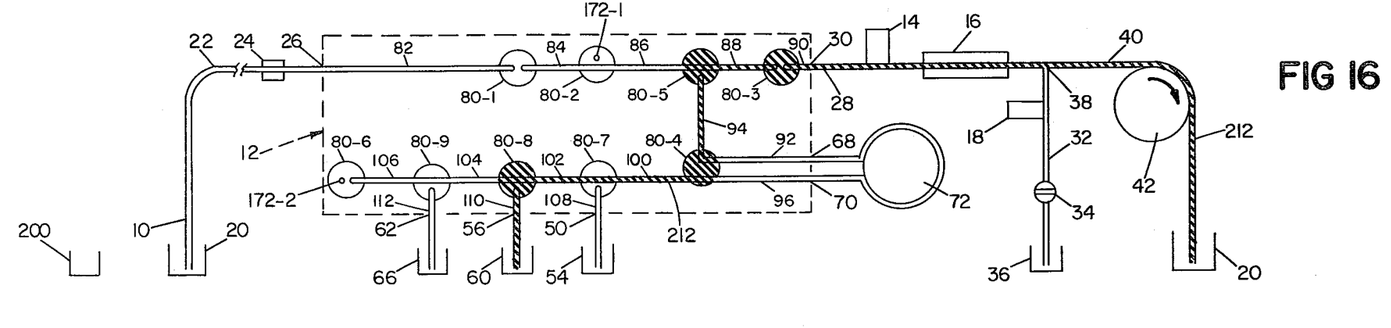

Calibration fluid from reservoir 60 or conditioning fluid from reservoir 66 may similarly be pumped through the analysis chambers of electrode systems 14 and 16. As indicated in FIG. 16, for example, by opening valve 80-8 rather than valve 80-7, calibration liquid 212 is pumped from the reservoir 60, the closed valve 80-7 providing complete isolation of calibration liquid 206. In operation, manifold vent valve 80-6 is first opened together with valves 80-4, 80-5 and 80-7, and pump 42 clears (dries) the entire manifold line (sections 94, 100, 102, 104 and 106). Valve 80-6 is then closed and valve 80-7 is opened so that liquid is pumped from reservoir 60 through the analysis chambers as indicated in FIG. 16. The flow of each such liquid may be segmented with air by operation of valve 80-6, as desired.

The analysis system provides efficient handling of small volumes of specimens to be analyzed. A blood or serum specimen of less than 200 microliters volume is analyzed while the volume of a urine specimen is about 700 microliters. Cross-contamination is minimized by the valve configurations, the manifold arrangement and the valve interconnections. Each liquid line can be pumped dry so that there is no liquid-liquid interface, and each has a valved vent to atmosphere. Each valve is easily cleaned and has low (essentially zero) residual volume.

While a variety of valve configurations are employed in the valve array 12, including valves of the flow through type such as valve 80-1, ported valves such as valve 80-2, T-valves such as valves 80-5 and 80-7 and by-pass valves such as valves 80-4, it will be apparent that other valve configurations may be obtained in accordance with the invention. Also, other liquid handling control configurations, such as the pumping of fluids with an array of valve type components, may also be obtained.

While particular embodiments of the invention have been shown and described, various modifications will be apparent to those skilled in the art, and therefore it is not intended that the invention be limited to the disclosed embodiments or to details thereof and departures may be made therefrom within the spirit and scope of the invention.

What is claimed is:

1. A valve comprising
   a valve body member having a firm and stable surface,
   a flexible valve sheet member having a surface for conforming and mating engagement with said valve body surface,
   backing plate structure,
   biasing means for resiliently clamping said sheet member between said body member and said backing plate structure,
   first and second channel portions in one of said members with a land portion between said channel portions, the surface of said land portion being coincident with the surface of the member in which it is located,
   and an actuator for flexing said sheet member between a first position in which said valve sheet surface is in mating and sealing engagement with said valve body surface to sealingly block flow between said first and second channel portions, and a second position in which said sheet surface is spaced away from said first position to allow flow between said first and second channel portions across said land portion.

2. The valve of claim 1 wherein said channel portions include a groove that extends along the surface of the member in which said land portion is located.

3. A valve comprising
   a valve body member having a firm and stable surface,
   a flexible valve sheet member having a surface for conforming and mating engagement with said valve body surface,
   first and second grooves extending along the surface of one of said members with a land portion located between the ends of said two grooves, the surface of said land portion being coincident with the surface of the member in which it is located,
   and an actuator for flexing said sheet member between a first position in which said valve sheet surface is in mating and sealing engagement with said valve body surface to sealingly block flow between said first and second grooves, and a second position in which said sheet surface is spaced away from said first position to allow flow between said first and second grooves across said land portion.

4. A valve comprising
   a valve body member having a firm and stable surface,
   a flexible valve sheet member having a surface for conforming and mating engagement with said valve body surface,
   first and second channel portions in one of said members with a land portion between said channel portions, the surface of said land portion being coincident with the surface of the member in which it is located, one of said channel portions being a flow through groove that extends along the surface of the member in which said land portion is located, and said land portion being located between said groove and an adjacent channel portion
   and an actuator for flexing said sheet member between a first position in which said valve sheet surface is in mating and sealing engagement with said valve body surface to sealingly block flow between said flow through groove and said adjacent channel portion, and a second position in which said sheet surface is spaced away from said first position to allow flow between said flow through groove and said adjacent channel portion across said land portion.

5. The valve of claim 4 wherein said adjacent channel portion is a second flow through groove that extends along the surface of the member in which said land portion is located, and said land portion is between said two grooves so that two separate flow through passages are isolated from one another when said valve sheet surface is in mating and sealing engagement with said valve body surface, and fluid is permitted to flow between said flow through passages across said land portion when said sheet surface is spaced away from said valve body surface.

6. The valve of claim 4 wherein said adjacent channel portion includes a port in the surface of the member in which said land portion is located, and said land portion is between said groove and said port so that said flow through passage is isolated from said adjacent channel portion when said valve sheet surface is in mating and sealing engagement with said valve body surface, and fluid is permitted to flow between said passage and said adjacent channel portion across said land portion when said sheet surface is spaced away from said valve body surface.

7. The valve of any one of claims 2-6 and further including backing plate structure, and means for clamping said sheet member between said body member and said backing plate structure, said backing plate structure having a circular opening such that a valve chamber of generally frustoconical configuration is provided when said actuator flexes said sheet member away from said body member.

8. The valve of any one of claims 1-6 wherein one of said members is transparent.

9. The valve of any one of claims 1-6 wherein said flexible sheet member is of a different color than the fluid to be controlled by said valve and said body member is transparent.

10. The valve of claim 1 wherein said flexible sheet member is softer and more resilient than said body member.

11. The valve of claim 10 wherein said flexible sheet member has a hardness of less than one hundred Shore A durometer.

12. The valve of claim 11 wherein said body member and said flexible sheet member are each of biologically inert material and are impermeable to the fluid to be controlled by said valve.

13. The valve of claim 1 wherein said actuator is adapted to flex said sheet member in a direction perpendicular to said stable surface of said body member.

14. The valve of claim 1 wherein said actuator includes a portion embedded in said sheet member.

15. The valve of claim 1 wherein said actuator has a cylindrical head embedded in said sheet member effective to stabilize the surface of said sheet member in the immediate vicinity of said land portion.

16. The valve of claim 1 wherein said actuator includes biasing means that acts to urge said sheet member into mating engagement with the surface of said body member.

17. The valve of any one of claims 1, 12 or 14 wherein the surfaces of said body member and said sheet member are planar.

18. A valve comprising a valve body member of transparent biologically inert material having a firm and stable planar surface, a flexible valve sheet member of biologically inert material having a planar surface for conforming and mating engagement with said valve body surface, backing plate structure, biasing means for resiliently clamping said sheet member between said body member and said backing plate structure, first and second channel portions in one of said members with a land portion between said channel portions, the surface of said land portion being coincident with the surface of the member in which it is located, and an actuator including a portion embedded in said sheet member for flexing said sheet member between a first position in which said valve sheet surface is in mating and sealing engagement with said valve body surface to sealingly block flow between said first and second channel portions, and a second position in which said sheet surface is spaced away from said first position to allow flow between said first and second channel positions across said land portion.

19. The valve of claim 18 wherein said backing plate structure has a circular opening such that a frustoconical valve chamber defined in part by the marginal surfaces of said circular opening is provided when said actuator flexes said sheet member away from said body member.

20. A valve array comprising a face plate body member having a firm and stable surface, a flexible valve sheet member having a surface for conforming and mating engagement with said valve face plate surface, backing plate structure, biasing means for resiliently clamping said sheet member between said body member and said backing plate structure, a network of channel portions in one of said members with a plurality of valve land portions, each said valve land portion being located between two adjacent ones of said channel portions, the surfaces of said land portions being coincident with the surface of the member in which they are located, and a plurality of actuators, each said actuator being arranged to flex said sheet member between a first position in which said valve sheet surface is in mating and sealing engagement with said valve face plate surface to sealingly block flow between adjacent ones of said channel portions, and a second position in which said sheet surface is spaced away from said first position to allow flow between said adjacent channel portions across the land portion corresponding to that actuator.

21. The valve array of claim 20 wherein said channel portions are in the surface of the member in which said land portions are located.

22. The valve array of claim 20 wherein said face plate member is of transparent material.

23. The valve array of claim 20 wherein each said actuator flexes said sheet in a direction perpendicular to said rigid surface of said face plate member.

24. The valve array of claim 20 wherein each said actuator has a portion embedded in said sheet member.

25. The valve array of claim 20 wherein each said actuator has a cylindrical head embedded in said sheet member effective to stabilize the surface of said sheet member in the immediate vicinity of each said land portion.

26. The valve array of either claim 20 or 25 wherein said flexible sheet member has a smooth continuous surface of a different color than the fluid to be controlled by said valves and said face plate member is transparent.

27. The valve array of claim 20 wherein each said actuator includes biasing means that acts to urge said sheet member into mating engagement with the surface of said face plate member.

28. The valve array of claim 20 wherein the mating surfaces of said face plate member and said sheet member are planar.

29. The valve array of claim 20 wherein said backing plate structure has a plurality of circular openings through which said actuators extend such that a frustoconical valve chamber defined in part by the marginal surfaces of said circular opening is provided when any one of said actuators flexes said sheet member away from said face plate member.

30. The valve array of claim 20 wherein said channel portions include a network of grooves that extends along the surface of said face plate member in which said land portions are located.

31. The valve array of claim 30 wherein said face plate member is of transparent material, said flexible sheet member has a smooth continuous surface of a different color than the fluid to be controlled by said valves and the mating surfaces of said face plate member and said sheet member are planar.

32. The valve array of claim 31 wherein said face plate member and said flexible sheet member are each of biologically inert material and are impermeable to the fluids to be controlled by said valve array, and said flexible sheet member is of less than one hundred Shore A durometer hardness.

33. The valve array of claim 32 wherein each said actuator has a cylindrical head embedded in said sheet member effective to stabilize the surface of said sheet member in the immediate vicinity of each said land portion, each said actuator includes biasing means that acts to urge said sheet member into mating engagement with the surface of said face plate member, and each said actuator is adapted to flex said sheet member in a direction perpendicular to said rigid surface of said face plate member.

* * * * *